US008824760B2

(12) United States Patent
Dennerlein et al.

(10) Patent No.: US 8,824,760 B2
(45) Date of Patent: Sep. 2, 2014

(54) MODIFICATION AND ELIMINATION OF BACK PROJECTION WEIGHT DURING THE CT IMAGE RECONSTRUCTION

(75) Inventors: Frank Dennerlein, Forchheim (DE); Frédéric Noo, Midvale, TN (US)

(73) Assignees: University of Utah Research Foundation, Salt Lake City, UT (US); Siemens Aktiengesellschaft, Munich (DE)

(*) Notice: Subject to any disclaimer, the term of this patent is extended or adjusted under 35 U.S.C. 154(b) by 1136 days.

(21) Appl. No.: 12/588,573

(22) Filed: Oct. 20, 2009

(65) Prior Publication Data

US 2011/0091085 A1    Apr. 21, 2011

(51) Int. Cl.
*A61B 6/03* (2006.01)
(52) U.S. Cl.
CPC ........................................ *A61B 6/03* (2013.01)
USPC .......................................................... 382/131
(58) Field of Classification Search
CPC ................ G06T 11/006; G06T 11/003; G06T 2207/10081; G06T 2211/421; G06T 11/008; A61B 6/032
USPC .......................................................... 382/131
See application file for complete search history.

(56) References Cited

U.S. PATENT DOCUMENTS

| | | | |
|---|---|---|---|
| 2006/0067457 A1* | 3/2006 | Zamyatin et al. | 378/4 |
| 2006/0120507 A1* | 6/2006 | Brunner et al. | 378/62 |
| 2007/0098134 A1* | 5/2007 | Toyoshima et al. | 378/4 |
| 2008/0123805 A1* | 5/2008 | Zellerhoff | 378/15 |

OTHER PUBLICATIONS

Dennerlein et al., Filtered Backprojection Reconstruction with depth-dependent Filtering, Presented Sep. 7, 2009 at the 10th International Meeting on Fully Three-Dimensional Image Reconstruction in Radiology and Nuclear Medicine, Proceedings of the 10th International Meeting on Fully Three-Dimensional Image Reconstruction in Radiology and Nuc.*
Sawyer et al., Implementation of Short-Scan Reconstruction with Compensation for Geometric Alignment for a Micro-CT System, 2004, IEEE, pp. 2981-2984.*
Dennerlein et al., Avoiding the backprojection weight in short-scan CT reconstruction, Presented Oct. 28, 2009 at the 2009 IEEE Nuclear Symposium, 2009 IEEE Nuclear Symposium Conference Record, pp. 2507-2509.*
Feldkamp et al., Practical cone-beam algorithm, 1984, Journal of the Optical Society of America A, vol. 1, No. 6, pp. 612-619.*
Katsevich, A general scheme for constructing inversion algorithms for cone beam CT, 2003, International Journal of Mathematics and Mathematical Sciences, vol. 2003, Issue 21, pp. 1305-1321.*
Principles of Computerized Tomographic Imaging IEEE Pres.. (c) Institute for Electrical and Electronic Engineers Avinash C. Kak, Malcolm Slaney; Book; 1988.

A. Katsevich, vol. 47, pp. 2583-2597 Analysis of an exact inversion algorithm for spiral cone-beam CT Phys. Med. Biol., 2002.
Y. Zou et. al. Exact image reconstruction on PI-lines from minimum data in helical cone-beam CT Phys. Med. Biol., vol. 49, pp. 941-959, 2004.
J. Pack et al., Cone-Beam Reconstruction Using the Backprojection of Locally Filtered Projections Med. Imag. vol. 24, No. 1, pp. 70-85, 2005; Jan. 1, 2005.
Meeting on Fully 3D Image Reconstruction in Radiology and Nuclear Medicine (Pittsburgh, PA), D. Townsend et al. Eds.; P. Danielsson et al. in Proc., pp. 141-144; 1997.
Med. Phys., vol. 30, No. 9, pp. 2493-2502; C. Bontus et al. A quasiexact reconstruction algorithm for helical CT using a 3-Pi acquisiton Med. Phys., vol. 30, No. 9, pp. 2493-2502, 2003; Sep. 1, 2003.
Phys. Med. Biol., vol. 49, No. 11, pp. 2129-2143; A. Katsevich, On two versions of a 3 algorithm for spiral CT Phys. Med. Biol., vol. 49, No. 11, pp. 2129-2143, 2004; Jun. 1, 2004.
IEEE Transaction Med. Imag. vol. 24, No. 8, pp. 977-986; C. Bontus et al. EnPiT: Filtered Back-Projection Algorithm for helical CT Using an n-Pi Acquisition IEEE Transaction Med. Imag. vol. 24, No. 8, pp. 977-986, 2005, Aug. 1, 2005.
Advances in Applied Mathematics, vol. 36, pp. 213-250; A. Katsevich Applied Mathematics Advances in Applied Mathematics, vol. 36, pp. 213-250, 2006.
IEEE Trans. Med. Imag., vol. 19, No. 9, pp. 848-863; R. Proska et al. The n-PI-Method for Helical Cone-Beam CT IEEE Trans. Med. Imag., vol. 19, No. 9, pp. 848-863, 2000.
Phys. med. Biol., vol. 49, pp. 2219-2238; D. Heuscher et al. Redundant data and exact helical cone-bema reconstruction Phys. med. Biol., vol. 49, pp. 2219-2238, 2004.
IEEE Trans. Med. Imag., vol. 25, No. 7, pp. 882-897; T. Köhler et al. The Radon-Split Method for Helical Cone-Beam CT and its Application to Nongated Reconstruction IEEE Trans. Med. Imag., vol. 25, No. 7, pp. 882-897, 2006.
IEEE Nuclear Science Symposium Conference Record, vol. 4, pp. 2264-2267; Zamyatin et al. Helical CT Reconstruction with Large Cone Angle IEEE Nuclear Science Symposium Conference Record, vol. 4, pp. 2264-2267, 2006.
Meeting on Fully 3D Image Reconstruction in Radiology and Nuclear Medicine, pp. 333-336; A. Katsevich et al, Beekman et al. Optimized reconstruction alogorithm for helical CT with fractional pitch between 1PI and 3PI Meeting on Fully 3D Image Reconstruction in Radiology and Nuclear Medicine, pp. 333-336, 2007; DE.

(Continued)

*Primary Examiner* — Toan Ton
*Assistant Examiner* — John Corbett
(74) *Attorney, Agent, or Firm* — Harness, Dickey & Pierce

(57) ABSTRACT

At least one embodiment of the invention relates to a method for the reconstruction of image data from an examined object, using measuring data, wherein the measuring data were first recorded during a relative movement between a radiation source on a computer tomography system and the examined object. In at least one embodiment, the image reconstruction is based on a back projection of the filtered measuring data. During the back projection, a back projection weight that depends on the respective image point is used and the power with which the back projection weight is used is selectable.

11 Claims, 5 Drawing Sheets

(56) References Cited

OTHER PUBLICATIONS

Phys. Med. Bio. vol. 49, pp. 2209-2218; Stierstorfer et al. Weighted FBP—a simple approximate 3D FBP algorithm for multislice spiral CT with good dose usage for arbitrary pitch Phys. Med. Bio. vol. 49, pp. 2209-2218, 2004.

Phys. Med. Biol. vol. 49, No. 13, pp. 2913-2931; H. Kudo et al. Exact and approcimate algorithms for helical cone-beam CT Phys. Med. Biol. vol. 49, No. 13, pp. 2913-2931, 2004; Jul. 1, 2004.

Med. Phys., vol. 31, No. 8, pp. 2230-2236; G. Shechter et al. The fequency split method for helical cone-beam reconstruction Med. Phys., vol. 31, No. 8, pp. 2230-2236, 2004; Aug. 1, 2004.

Med. Phys., vol. 34, No. 6, pp. 1989-1998; X. Tang et al., Handling dara redundancy in helical cone beam reconstruction with a cone-angle-based window function and its asymptotic approximation Med. Phys., vol. 34, No. 6, pp. 1989-1998, 2007; Jun. 1, 2007.

Meeting on Fully 3D Image Reconstruction in Radiology and Nuclear Medicine, pp. 120-123; H. Schöndube et al. F. Beekman et al. Towards an Efficient Two-Step Hilbert Algorithm for Helical Cone-Beam CT, 2007.

IEEE Nuclear Science Symposium Conference Record NSS '07, vol. 6, pp. 4467-4471; IEEE Nuclear Science Symposium Conference Record NSS '07, Comparative evaluation of two analytical methods for Helical Cone-Beam Tomography vol. 6, pp. 4467-4471, 2007 H. Schöndube, K. Stierstorfer, F. Dennerlein; 2007.

Reconstruction Algorithms for Computed Tomography; Claas Bontus and Thomas Koehler; Reconstruction Algorithms for Computed Tomography; Advances in Imaging and Electron Physics, vol. 151.

Accurate helical cone-beam CT reconstruction with redundant data; Harald Schöndube, Karl Stierstorfer, Federic Noo; "Accurate helical cone-beam CT reconstruction with redundant data", 2009 Institute of Physics and Engineering in Medicine, Phys. Med.Biol.54 (2009) 4625-4644.; 2009.

Exact cone-beam CT with a spiral scan; Exact cone-beam CT with a spiral scan, K. Tam, S. Samarasekera and F. Sauer, Phys. Med. Biol. vol. 43, pp. 1015-1024, 1998.

Fan-Beam Filtered-Backprojection Reconstruction without Backprojection Weight F. Dennerlein, F. Noo, J. Hornegger, G. Lauritsch; Others; Physics in Medicine and Biology; vol. 52, No. 11, pp. 3227-3240, May 15, 2007.

* cited by examiner

MODIFICATION AND ELIMINATION OF BACK PROJECTION WEIGHT DURING THE CT IMAGE RECONSTRUCTION

FIELD

At least one embodiment of the invention generally relates to a method for the reconstruction of image data from an examined object using measuring data, wherein the measuring data were recorded by a computer tomography system.

BACKGROUND

Methods for scanning an object to be examined with a CT system are generally known and utilize, for example, circular scans, sequential circular scans with forward movement or spiral scans. Other types of scans which are not based on circular movements are also possible, for example scans with linear segments. Absorption data from the examined object are recorded from different recoding angles using at least one X-ray source and at least one opposite-arranged detector, and the absorption data or projections collected in this way are then used for computing sectional images through the examined object with the aid of corresponding reconstruction methods.

Methods for the image reconstruction are generally used for the reconstruction of computer-tomography images from X-ray CT data sets recorded by a computer tomography device (CT device), meaning data from the recorded projections, wherein these methods are based on a back projection of the filtered measuring data. One of the standard methods used nowadays is the so-called filtered back projection technique (FBP), for which data are detected and are then transformed to the frequency range. A filtering occurs in the frequency range and the filtered data are subsequently transformed back. With the aid of the filtered data, a back projection is then realized to the individual voxels within the volume of interest.

One problem with the image reconstruction method based on the back projection of filtered measuring data is that when using the fan-beam or the cone-beam geometry for the measuring operations, a back projection weight is used which depends on the location of the image point or pixel that is to be computed. This local variance in the back projection weight leads to undesirable image characteristics because the image noise and the local resolution are not distributed uniformly, but non-homogeneously throughout the image.

One remedy for this problem is to use a rebinning, for which a so-called "rebinning" step is carried out following the data detection. In this step, the data generated by the beam that is spreading in the manner of a fan once it leaves the source, are rearranged so as to resemble X-ray beams with parallel rays impinging on the detector.

It is the object of the present invention to provide a reconstruction method for CT images, which delivers high image quality even if a rebinning step is omitted. The object is furthermore to provide a corresponding computer and control unit, a CT system, a computer program and a computer program product.

SUMMARY

In at least one embodiment, a method is disclosed, as well as a computer and control unit, a CT system, a computer program and a computer program product. Advantageous embodiments and modifications form the subject matter of dependent claims.

With the method according to at least one embodiment of the invention for reconstructing image data from an examined object, using measuring data, the measuring data were initially recorded during a relative movement between a radiation source belonging to a computer tomography system and the examined object. The image reconstruction is based on a back projection of the filtered measuring data, for which a back projection weight is used that depends on the location of the respective image point. The power used for the back projection weight can be selected.

Standard methods can be used for recording the data, in particular also including a rotational movement of the radiation source around the object to be examined. However, other types of movements are possible as well. A detector is arranged opposite the radiation source, on the other side of the object to be examined, which detects the X-ray radiation emitted by the radiation source.

The algorithm used for reconstructing image data from the measured data, in at least one embodiment, comprises at least two steps: a filtering of the measuring data and a back projection of the measuring data. These include many of the currently used methods, in particular the classic fan-beam FBP reconstruction (FBP=filtered back projection) and the Feldkamp algorithm for the C-bend CT, as well as algorithms that are similar to the Feldkamp algorithm for the spiral CT or the precise reconstruction methods used for helical scans according to the method disclosed in Katsevich et al.

A back projection weight is used during the back projection step for weighting the previously filtered measuring data. The back projection weight differs for each location and depends on the location of the image point for which the image value is computed with the respective back projection step. It means that the back projection weight can have a different value from image point to image point.

The back projection weight enters with a specific power into the back projection step. This power can be selected, meaning a general formula is available for use with the image reconstruction which can be changed by selecting the power for the back projection weight in the back projection step. If the back projection weight is to be entered squared, meaning to the 2nd power, then a selectable parameter in the formula is determined such that the back projection weight enters to the 2nd power into the back projection step. Of course, a power other than to the 2nd power can also be selected, in particular to the 0 power. In that case, the back projection weight used does not vary with the location because of the special selection in the back projection step.

According to one modification of at least one embodiment of the invention, the measuring data are filtered with a differentiation according to the method of finite differences, using supporting points and in particular two supporting points, wherein the distances between the supporting points comprise a term that depends on the respective location of the image point and corresponds to the back projection weight and that the power of this term follows from the power of the back projection weight.

For the differentiation according to at least one embodiment of the method of finite differences, the value of a function is computed at specific supporting points and the difference determined between the values of adjacent supporting points. This distance between adjacent supporting points depends on the location of the image point for which the image value is computed. The dependence is caused by a term that corresponds to the back projection weight, wherein the correspondence in particular can mean that the term—except for its power—is identical to the back projection weight. However, it is also possible that the term coincides with the back projection weight only with respect to the expression that expresses the dependence on the location.

The powers of the term and the back projection weight are not independent on each other. Rather, the power of the term is fixed as soon as the power of the back projection weight is selected. Of course the reverse sequence for determining the powers can also be used. It is particularly advantageous if the power of the back projection weight is 2−p and the power of the term is p, wherein p can be selected.

For the second method according to at least one embodiment of the invention for reconstructing image data from an examined object using measuring data, the measuring data were also first recorded during a relative movement between a radiation source on a computer tomography system and the object to be examined. As with at least one embodiment of the first method, the image reconstruction in this case is also based on a back projection of the filtered measuring data. For the filtering of the measuring data, a differentiation is realized based on the method of the finite differences and using supporting points, especially two supporting points, wherein the distances between the supporting points depend on the location of the respective image point. The back projection occurs without using a back projection weight that depends on the location of the respective image point.

The above explanations provided for the first method according to at least one embodiment of the invention are valid and correspondingly also apply to its embodiments and modifications.

With at least one embodiment of the second method, the power of the back projection weight cannot be selected. Rather, such a back projection weight is not used, meaning its power is equal to zero. In particular, we can arrive at this by using the first method and correspondingly selecting the power for the back projection.

According to an embodiment of the invention, the dependence on the location of the respective image point stems from the expression $\underline{x} \cdot \underline{e}_w$, wherein $\underline{x}$ indicates the location of the respective image point and $\underline{e}_w$ indicates a direction perpendicular to the surface of the detector. This is true for the location dependence of the back projection weight as well as the location dependence during the differentiation step.

Less than one complete rotation may have been used for obtaining the measuring data recorded during a relative movement of the radiation source around the object to be examined. Accordingly, it is not necessary to have measuring data from all viewing directions of the radiation source onto the object to be examined for the image reconstruction. For example, measuring data from a projection angle range of 240° would be sufficient for a rotational movement.

The measuring data may have been recorded with the fan-beam geometry, allowing two-dimensional image data of the examined object to be reconstructed. Alternatively, the measuring data may have been recorded with cone-beam geometry, allowing three-dimensional image data of the examined object to be reconstructed.

It is especially advantageous if the image reconstruction from the measuring data is realized without a prior conversion to the parallel-beam geometry, which saves computation expenditure, increases the image sharpness and reduces the waiting time before the reconstructed image is available.

The computer and control unit according to at least one embodiment of the invention is used for the reconstruction of image data from an examined object, using measuring data from a CT system. The unit comprises a program memory for storing program code, wherein the program code stored therein—if applicable among other things—is suitable for realizing a method of the above-described type. The CT system according to at least one embodiment of the invention comprises such a computer and control unit. The unit can furthermore comprise other components, for example those required to record the measuring data.

The computer program according to at least one embodiment of the invention is provided with program code segments which are suitable for realizing the above-described method, provided the computer program is executed on a computer.

The computer program product according to at least one embodiment of the invention comprises program code segments stored on a computer-readable data carrier and suitable for realizing the above-described method, provided the computer program is executed on a computer.

BRIEF DESCRIPTION OF THE DRAWINGS

The invention is explained further in the following with the aid of example embodiments, showing in.

DETAILED DESCRIPTION OF THE EXAMPLE EMBODIMENTS

Figure 1:
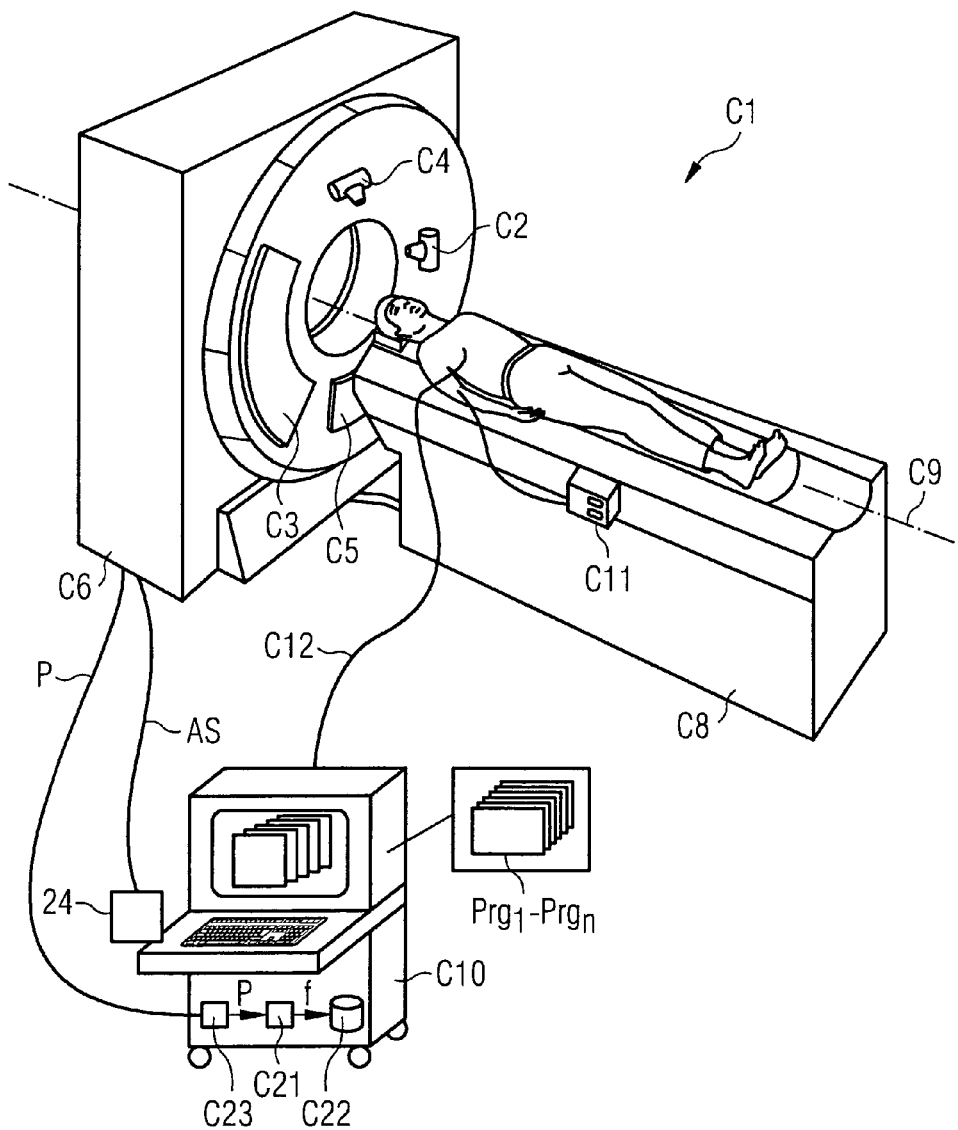
FIG. 1: A first schematic representation of an example embodiment of a computer tomography system with image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 illustrates a first computer tomography system C1, shown schematically together with an image reconstruction device C21. A closed gantry, not shown herein, is located inside the gantry housing C6 with thereon arranged first X-ray tube C2 and an opposite-arranged detector C3. A second X-ray tube C4 with opposite-positioned detector C5 is optionally arranged on the CT system shown herein. As a result, an additional radiator/detector combination is made available which makes it possible to achieve a higher time resolution or to carry out "dual energy" examinations in the radiator/detector systems when using different X-ray energy spectra.

The CT system C1 furthermore comprises a patient gurney C8 on which a patient can be moved along a system axis C9, also called a z-axis, during the examination. However, the scan can also be realized as a pure circular scan without forward movement of the patient and exclusively in the region of interest to the examination. In that case, the X-ray source C2 or C4 respectively rotates around the patient to record the measuring data which are used for the reconstruction of sectional images, wherein the detector C3 or C5 also rotates along on the opposite side of the X-ray source C2 or C4. As an alternative to a sequential scan where the patient is pushed step-by-step through the examination field between the individual scans, it is of course also possible to realize a spiral scan for which the patient during a rotating scanning operation with X-ray radiation is also pushed continuously along the system axis C9 through the examination field between the X-ray tube C2 or C4 and the detector C3 or C5. As a result of the movement of the patient along the axis C9 and the simultaneous rotation of the X-ray source C2 or C4, a spiral scan result for the movement of the patient relative to the X-ray source C2 or C4 during the measuring operation along a helical path. This helical path can also be achieved by moving the gantry along the axis C9 while the patient is not moved.

The CT system 10 is controlled with a computer and control unit C10, using a computer program code $Prg_1$ to $Prg_n$ that is stored and present in a memory. Starting with the computer and control unit C10, acquisition control signals AS can be transmitted via an interface 24 for actuating the CT system C1 according to specific measuring protocols.

The projection measuring data p (henceforth also called raw data) acquired by the detector C3 or C5 are transmitted via a raw data interface C23 to the computer and control unit C10. These raw data p are then processed further in an image reconstruction component C21, if necessary following a suitable pre-processing. The image reconstruction component C21 is realized for this example embodiment in the computer and control unit C10 in the form of software on a processor, e.g. in the form of one or several computer program codes $Prg_1$ to $Prg_n$. Once reconstructed with the aid of the image reconstruction component C21, the data f are then stored in a memory C22 of the computer and control unit C10 or are displayed in the standard manner on the monitor for the computer and control unit C10. However, the data can also be fed via an interface, not shown in FIG. 1, into a network that is connected to the computer tomography system C1, for example a radiological information system (RIS), where the data are stored in a mass memory or displayed in the form of images.

The computer and control unit C10 can additionally also carry out the function of an ECG, wherein a line C12 is used for discharging the ECG potentials between the patient and the computer and control unit C10. In addition, the CT system C1 that is shown in FIG. 1 also comprises a contrast-element injection device C11 for additionally injecting contrast elements into the blood circulation of the patient, so that the vessels of a patient, in particular the chambers of the beating heart, can be shown in further detail. The option furthermore exists of carrying out perfusion measurements, for which the proposed method is also suitable.

Figure 2:
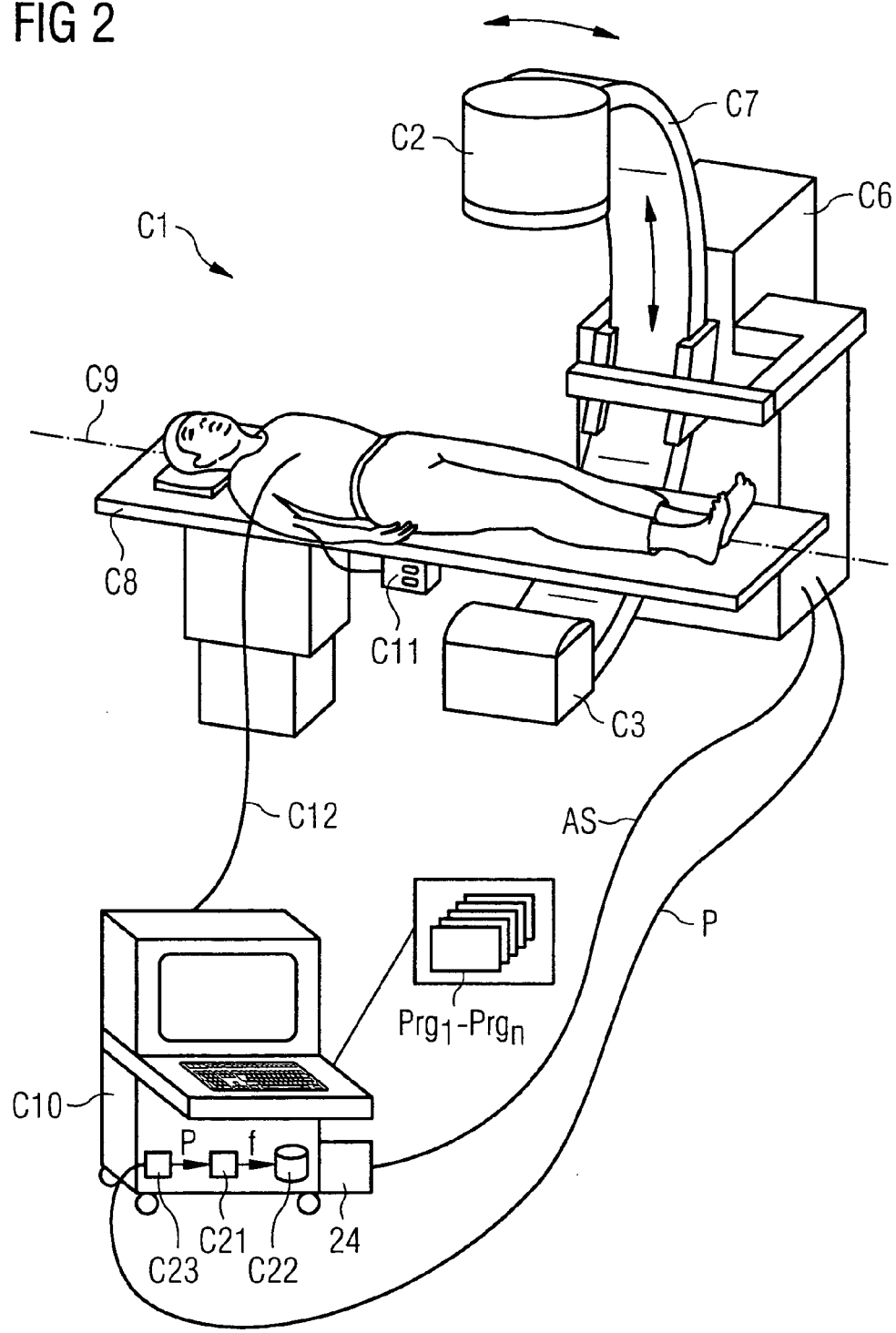
FIG. 2: A second schematic representation of an example embodiment of a computer tomography system with image reconstruction component.

FIG. 2 shows a C-bend system where in contrast to the CT system shown in FIG. 1 the housing C6 carries the C-bend C7 on which the X-ray tube C2 is mounted on one side and the detector C3 on the opposite side. The C-bend C7 is also pivoted around a system axis C9 for the scanning, so that a scanning is possible from a plurality of scanning angles and so that corresponding projection data p can be determined from a plurality of projection angles. In the same way as the CT-system in FIG. 1, the C-bend system C1 in FIG. 2 is also provided with a computer and control unit C10 of the type as described for FIG. 1.

Embodiments of the invention can be used in both systems shown in FIGS. 1 and 2, and, in principle, can also be used in other CT systems, for example CT systems provided with a detector embodied as a complete ring.

Figure 3:
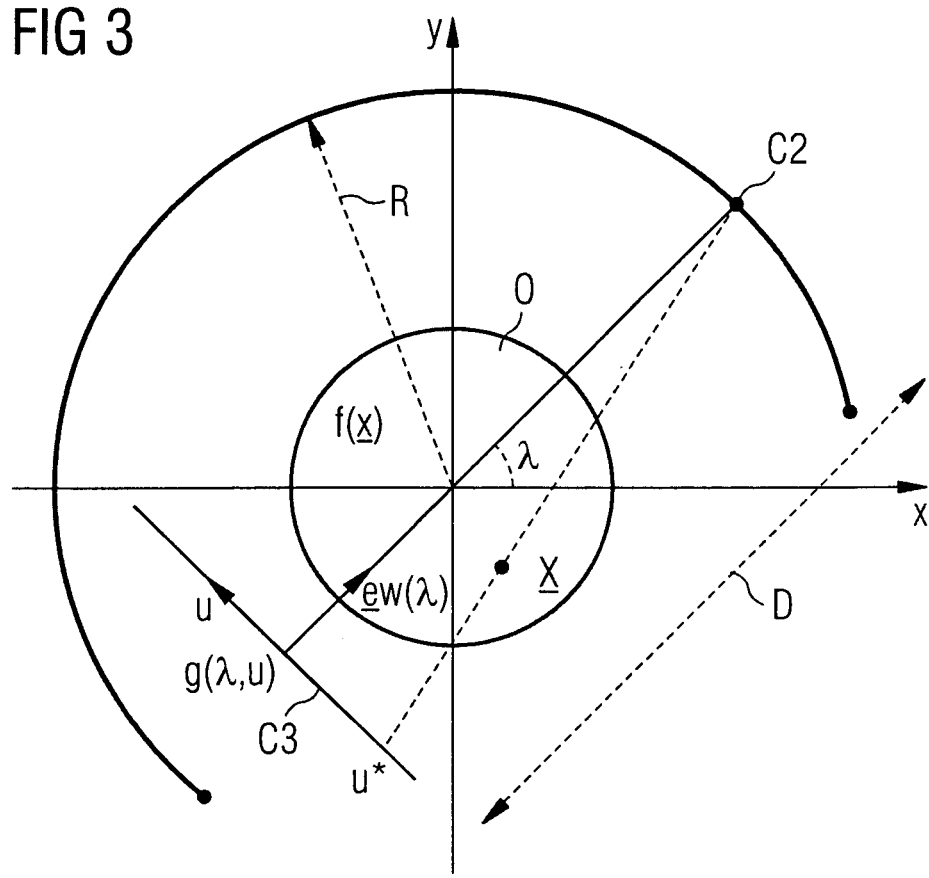
FIG. 3: The recording geometry for fan-beam recordings.

FIG. 3 shows the recording geometry for CT fan-beam recordings. To simplify matters, the following explanation is based on the fan-beam geometry, for which a single detector row with a plurality of detector elements is used. Two-dimensional image data of the examined object are reconstructed from the recorded projections, meaning from the measuring data. The following explanations can be used in an analog manner for determining three-dimensional image data when using the cone-beam geometry for the measuring. In that case, the detector used is provided with a plurality of detector rows.

The X-ray beams transmitted by the X-ray source C2 are fan shaped when they arrive at the planar detector C3. The detector C3 comprises a large number of side-by-side arranged detector pixels or elements, which are numbered with the index u. On the path from the X-ray source C2 to the detector C3, the X-ray beams pass through the object to be examined O, for which the density distribution is f(x). The plane containing the image to be detected—which corresponds to the density distribution f(x)—is spanned by the axes x and y. These two axes are positioned perpendicular to the system axis C9 of the FIGS. 1 and 2. The point of intersection of the axes x and y represents the rotational point or fulcrum, around which rotates the system including X-ray source C2 and detector C3. The spacing between the rotational point and the X-ray source C2, also called the scan radius, is given the reference R while the distance between the X-ray source C2 and the detector C3 is given the reference D.

The projection angle is given the reference $\lambda$. For each projection angle $\lambda$, each detector element records a measuring data value with index u. The resulting measuring data are g($\lambda$, u). The projection of the point x from the examined object O onto the detector C3, meaning the connection between the X-ray source C2 and the detector C3 through the point x is the detector element u*. The detector normal, meaning the direction perpendicular to the detector C3, for the respective projection angle $\lambda$ is ew ($\lambda$).

Essential for a CT X-ray system is the image reconstruction algorithm, which is used to compute from the acquired projection data a representation of the object density f(x) and thus makes possible in the first place numerous modern medical applications. The capacity of the total system is consequently determined substantially by the quality of the reconstruction algorithm that is used. For example it would be a poor choice to select algorithms that do not deliver a uniform distribution of image noise and local resolution in the image region that is of interest, the so-called region of interest (ROI), rather than algorithms for which these two essential image characteristics are distributed uniformly over the ROI.

Reconstruction algorithms for the cone-beam geometry or the fan-beam geometry, which are based on the back projection of filtered projection data (essentially all algorithms used nowadays, including the Feldkamp algorithm), require a weighting factor that varies with the location during the back projection, the so-called back projection weight. With the fan-beam geometry, the density distribution f(x) is computed from the measuring data g($\lambda$, u) during the classic FBP (filtered back projection) according to the equation (1), wherein the nomenclature orients itself on the representation in FIG. 3:

$$f(x) = \int_\Lambda d\lambda \frac{RD}{|R - \underline{x} \cdot \underline{e}_w(\lambda)|^2} \times \int_{-\infty}^{\infty} du h_r(u^* - u) \frac{D}{\sqrt{u^2 + D^2}} w(\lambda, u) g(\lambda, u) \quad (1)$$

w ($\lambda$, u) is a weighting function, which takes into account redundancies in the measuring data, wherein a Parker weighting can be used for this.

$h_r$ (u) is the ramp filter core for which a Shepp-Logan filter can be used.

$$\frac{D}{\sqrt{u^2 + D^2}}$$

is the cosine weight that takes into account the geometric conditions during the data processing.

The inner integral, meaning the integration over u, represents a convolution for which a specific projection image g($\lambda$, u) is high-pass filtered with the projection angle $\lambda$.

With the outer integral, meaning the integration via $\lambda$, all convoluted projection images are projected into the image volume and are weighted and summed up with $$\frac{RD}{|R - \underline{x} \cdot \underline{e}_w(\lambda)|^2}.$$

This step is the back projection into the local space. The integration takes place for all projections, wherein $\Lambda$ refers to the total projection angle region, meaning the scanning region in which data were recorded.

The back projection weight is $|R-\underline{x}\cdot\underline{e}_w(\lambda)|^2$. It means that when computing the density value f(x) of the point x, the position of this point is taken into consideration. Accordingly, the back projection weight is dependent on the location. This weight causes heterogeneous image characteristics, wherein the noise and local resolution in particular vary considerably. A diagnosis or an automatic further processing of the reconstruction result is made difficult by these non-homogeneities.

One option for improving the image quality, which is used for example in the diagnostic CT, is to convert the recorded data into a parallel geometry through interpolating and re-sorting of the data. This step is referred to as rebinning. With the reconstruction in the parallel geometry, the back projection weight is omitted, so that the noise and the local resolution in the images become very uniform. However, the rebinning has several disadvantages:

the computing expenditure is increased by this additional step since new data must first be computed from the measured data with the aid of interpolation;
the interpolation leads to a loss in resolution;
the image reconstruction can take place only following a completion of the acquisition because the measuring data from all the projections must be available before these can be combined with the aid of rebinning.

It would therefore be desirable to use an algorithm for the direct reconstruction in the cone-beam geometry or the fan-beam geometry—meaning without rebinning—for which the back projection weight can be changed optionally or can be eliminated completely, so that the image quality of the reconstruction result is improved with respect to homogeneity of image noise and local resolution.

A fan-beam reconstruction algorithm without back projection weight was recently introduced by Dennerlein et al in the publication F. Dennerlein, F. Noo, G. Lauritsch, J. Hornegger: "Fan-beam filtered-backprojection reconstruction without backprojection weight," Phys. Med. Biol., Vol. 52, No. 11, pages 3227-3239, 2007, wherein this algorithm can be used for the case of a full-circle data recording. As expected, this method delivers improvements in the image quality. Unfortunately, it cannot be used for the partial circle reconstruction, which is given the highest importance nowadays. A partial-circle reconstruction is understood to mean that measuring data are recorded over a projection angle of less than 360°. This is advantageous for increasing the time resolution and reducing the radiation dose.

Several mathematical reformulations are made. First of all, the following identity is used:

$$h_r(u) = \frac{1}{2\pi} \frac{\partial}{\partial u} h_h(u) \quad (2)$$

For this, $h_h(u)$ represents the core of the Hilbert transformation. The ramp filter core can thus be written as Hilbert transformation core.

By using the equation (2), the equation (1) can be rewritten as follows:

$$f(\underline{x}) = \frac{1}{2\pi} \int_\Lambda d\lambda \frac{RD}{|R - \underline{x} \cdot \underline{e}_w(\lambda)|^2} \times \int_{-\infty}^{\infty} du \delta'(u^* - u) g_H(\lambda, u) \quad (3)$$

In this case, δ' stands for the derivative of the Dirac delta function, and $$g_H(\lambda, u) = \int_{-\infty}^{\infty} du' h_h(u - u') \frac{D}{\sqrt{u'^2 + D^2}} w(\lambda, u') g(\lambda, u') \quad (4)$$

wherein gH represents the weighted and Hilbert filtered measuring data.

The following change is made in the variables:

$$u = \frac{D^p}{|R - \underline{x} \cdot \underline{e}_w(\lambda)|^p} l \quad (5)$$

and $$du = \frac{D^p}{|R - \underline{x} \cdot \underline{e}_w(\lambda)|^p} dl$$

The inner integral of the equation (3) can now be written as follows, using the new variable l, meaning using the equation (5), in the following form:

$$\int_{-\infty}^{\infty} du \delta'(u^* - u) g_H(\lambda, u) = \quad (6)$$

$$\frac{|R - \underline{x} \cdot \underline{e}_w(\lambda)|^p}{D^p} \times \int_{-\infty}^{\infty} dl \delta'(l^* - l) g_H\left(\lambda, \frac{D^p l}{|R - \underline{x} \cdot \underline{e}_w(\lambda)|^p}\right)$$

In the process, the relationship between l* and u* is the same as between l and u; see equation (5).

We arrive at the right side of the equation (6) by utilizing the homogeneity characteristics of the function δ', wherein the following applies:

$$\delta'(tu) = \frac{1}{t^2} \cdot \delta'(u)$$

meaning the factor t can be pulled inverted and squared from the function.

The integral on the right side of the equation (6), the convolution with the function δ' represents a derivative. The result of this operation can be obtained numerically via a differentiation according to the method of the finite differences, meaning by computing the function gH at two locations that are close together, the supporting points, and determining the difference thereof. (Several supporting points can also be used in place of two supporting points.) The following is defined for this:

$$g_F(\lambda, u^*, \Delta l) := \quad (7)$$

$$\frac{1}{2\Delta l}\left(g_H\left(\lambda, u^* + \frac{D^p \Delta l}{|R - \underline{x} \cdot \underline{e}_w(\lambda)|^p}\right) - g_H\left(\lambda, u^* - \frac{D^p \Delta l}{|R - \underline{x} \cdot \underline{e}_w(\lambda)|^p}\right)\right)$$

In this case, Δl is a parameter that can be selected and does not refer to the distance between the two supporting points since Δl must still be multiplied with the scaling factor for the distance determination. Δl is a parameter of the algorithm which controls the global tradeoff between local resolution and noise in the resulting image. For that reason, Δl has a similar function as the apodizing of the ramp core in the classic method. A small Δl means a high resolution while a large Δl means a low resolution. The value of Δl should be approximately in the range of the sampling density of the detector or the image grid.

If we insert this into the equation (6) and then insert this equation into the equation (3), we obtain the following:

$$f(\underline{x}) = \frac{1}{4\pi\Delta l} \int_\Lambda d\lambda \frac{RD^{(1-p)}}{|R - \underline{x} \cdot \underline{e}_w(\lambda)|^{(2-p)}} g_F(\lambda, u^*, \Delta l) \quad (8)$$

The equation (8) can then be used in place of the classic FBP method for the image reconstruction. Whereas in the equation (3), meaning the classic FBP, the back projection weight has the power 2, this is now written in equation (8) as: $|R - \underline{x} \cdot \underline{e}_w(\lambda)|^p$, meaning it has the power (2−p), wherein p can be selected in this case. By selecting p=2, the back projection weight is eliminated completely. An FBP algorithm has thus been provided, which can function without the location-variant back projection weight. In addition, the equation (8) makes possible a free modification of the back projection weight since p can be selected optionally per se.

The ability to modify the back projection weight is of high importance for the quality of the reconstructed image. As previously explained, the back projection weight results in an inhomogeneous distribution of noise and local resolution within the image.

The locality variant expression $|R - \underline{x} \cdot \underline{e}_w(2)|$ is contained in the derivative calculation when selecting p≠0. In particular, when selecting p=2, this expression is contained exclusively in the derivative and not in the back projection weight. Within the derivation derivative calculation, the term $|R - \underline{x} \cdot \underline{e}_w(\lambda)|^p$ determines how large the distance between the adjacent supporting points is when computing the finite difference. This distance is consequently different from point to point within the image or the examined object. In contrast to the location-dependent back projection weight, this does not cause a negative change in the reconstructed image.

Figure 5A:
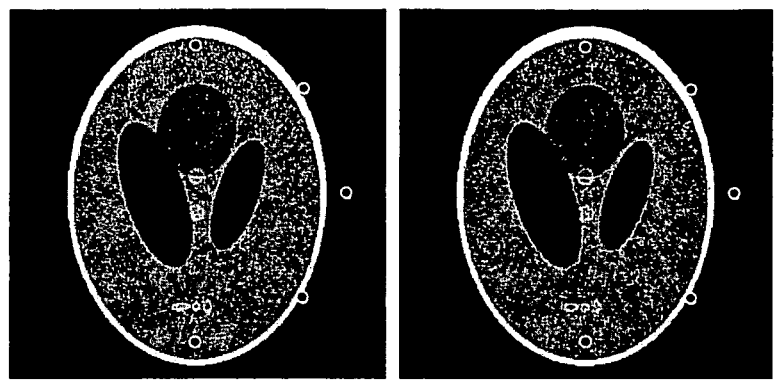
FIG. 5: Two CT images and the associated local resolution.
Figure 5:
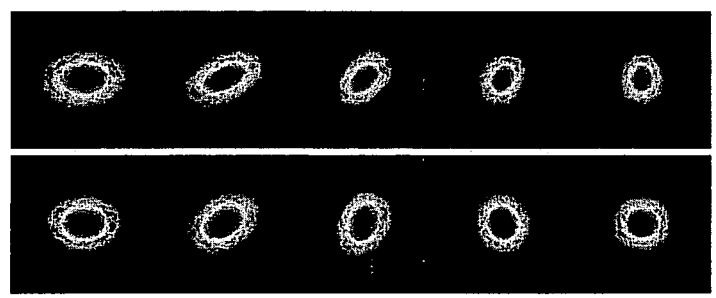

The described steps make available a new reconstruction formula for the fan-beam geometry and the cone-beam geometry. The new formulas have the following advantages as compared to the traditional formulas:

the back projection weight can be modified optionally;
the back projection weight can be avoided completely;

the formulas are valid for the partial circle and the full circle measuring operations;

simulation studies—see also the following description to FIG. 5—prove that the formulas deliver a much more uniform distribution of the local resolution over the examined ROI;

simulation studies—see the following description to FIG. 4 for this—prove that the formulas provide a much more uniform distribution of the image noise over the examined ROI;

the new formulas can be incorporated quite easily into existing reconstruction environments and this requires only slight modifications.

With the proposed methods, the back projection weight can be changed optionally for each analytical reconstruction method for the partial circle and the full circle geometry, provided the reconstruction method is based on the back projection of filtered data and provided the filtering step prior to the back projection can be formulated as derivative calculation. This applies to many known reconstruction methods, for example the Feldkamp algorithm, the classic fan-beam reconstruction formula, the spiral CT approaches etc. In particular, the back projection weight can be eliminated completely, so that we obtain a new reconstruction formula without back projection weight for the full circle and the partial circle reconstruction. In the process, the method is not restricted to circular source trajectories, but can also be used with other geometries, e.g. the rectangular source trajectories.

To check the improvement in the image noise and the local resolution, images were reconstructed from CT measuring data sets, obtained on the one hand with traditional FBP methods (see equation (3)) and on the other hand with the new method (see equation (8)) by using p=2. A two-dimensional Shepp-Logan Phantom was used as examination object, which represents a section through a human skull, wherein $\Delta l=0.2$ was selected for the new method. The two algorithms were adapted to each other in such a way that the local resolution of the reconstructed images is the same in the iso-center. For this, the ramp filter core for the classic FBP method was provided with a suitable band width limitation and a smoothing near the band limit.

Figure 4A:
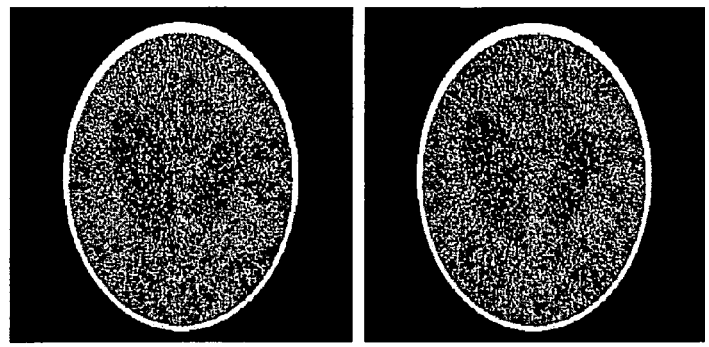
FIG. 4: Two CT images and the associated image noise.
Figure 4B:
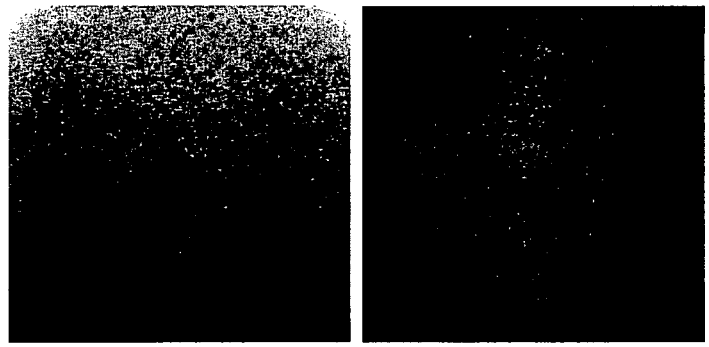

FIG. 4 demonstrates the effect of the improvement in the homogeneity of the noise. FIG. 4A illustrates two reconstructed images, wherein the left image was obtained with the classic FBP and the right image with the new method using p=2. The two images arranged below in FIG. 4B show the standard deviations within the images, which corresponds to the image noise. It can be seen that the left part of FIG. 4B, which corresponds to the classic FBP method, has a standard deviation extending from the top toward the bottom, which does not exist in the right part of FIG. 4B that corresponds to the new method.

Figure 4C:
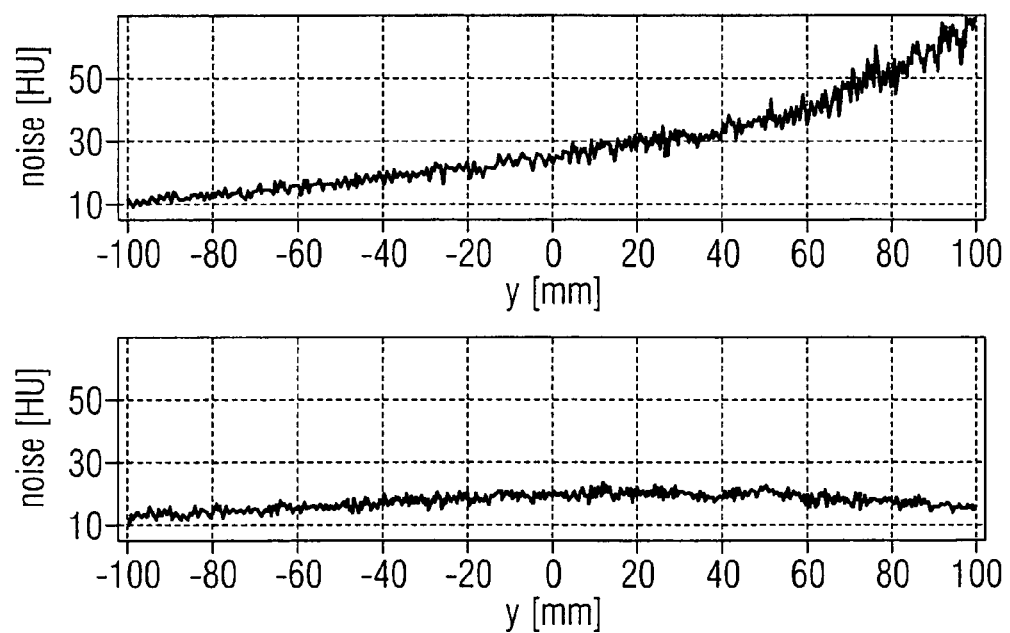

Along the y-axis that extends in FIG. 4A and FIG. 4B through the center from the top toward the bottom and for which the course is plotted in 4C toward the right in mm, FIG. 4C shows the change in the standard deviation noise in HU (Hounsfield Units). The representation on the top in FIG. 4C corresponds to the classic FBP method. It is clearly visible that the image noise increases from the bottom toward the top. The lower representation in FIG. 4C corresponds to the new method and clearly shows that there is no change in the image noise from the bottom toward the top. It means that the image noise is homogeneous for the new method.

FIG. 5 demonstrates the effect of the improvement in the homogeneity of the local resolution. FIG. 5A shows two images, wherein the left image corresponds to an averaging of the images won using the classic FBP method and the right image represents an averaging of the images obtained with the new method. The local resolution is determined at the 5 locations marked with crosses by determining a point-spread function at the respective location. These point-spread functions are shown in FIG. 5B, wherein the upper portion of FIG. 5B corresponds to the classic FBP method and the lower portion to the new method. It can be seen clearly that the point-spread functions of the upper part of FIG. 5B are different from point to point. However, the point-spread functions in the lower part of the FIG. 5B resemble each other closely, which corresponds to a high similarity of the local resolution at the different locations on the images obtained with the new method and thus corresponds to an increased homogeneity of the local resolution as compared to the classic FBP method.

With the aid of FIGS. 4 and 5, it was demonstrated that for the case where p=2, meaning where the back projection weight is omitted, a clear increase in the homogeneity of the image noise and the local resolution can be achieved. Even for other p values where the back projection weight is not omitted but is used with a different power than the one used for the known methods, an increase in the homogeneity of these variables can occur as compared to the known methods.

The invention was described in the above with the aid of an example embodiment. However, it is understood that numerous changes and modifications are possible without leaving the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the reconstruction of image data of an examined object from measuring data, the measuring data being recorded with a detector during a relative movement between a radiation source of a computer tomography system and the examined object, the method comprising:
   basing the image reconstruction on a back projection of filtered measuring data;
   realizing the back projection using a back projection weight which depends on a location of a respective point of the image data; and
   selecting a power with which the back projection weight is used, wherein
      a differentiation according to the method of the finite differences is realized, using supporting points for filtering the measuring data,
      a distance between supporting points contain a term that depends on the location of the respective image point and corresponds to the back projection weight, and
      a power of the term follows from the selected power of the back projection weight.

2. The method according to claim 1, wherein the power of the back projection weight is 2−p and the power of the term is p, and
   p has a selectable nonzero value.

3. The method according to claim 1, wherein the dependence on the location ($\underline{x}$) of the respective image point is derived from the term $\underline{x} \cdot \underline{e}_w$ wherein $\underline{x}$ indicates the location ($\underline{x}$) of the respective image point and $\underline{e}_w$ indicates a direction perpendicular to the surface of the detector.

4. The method according to claim 1, wherein the measuring data are recorded during a relative movement of the radiation source around the examined object, and
   the movement amounts to less than one complete rotation.

5. The method according to claim 1, wherein the measuring data are detected in a fan-beam geometry and used for reconstructing two-dimensional image data of the examined object.

6. The method according to claim 1, wherein the measuring data are detected in a cone-beam geometry and used for reconstructing three-dimensional image data of the examined object.

7. The method according to claim 1, wherein the image reconstruction from the measuring data is realized without prior conversion to the parallel beam geometry.

8. The method according to claim 1, wherein the using of supporting points includes using two supporting points.

9. A computer and control unit for reconstruction of image data of an examined object from measuring data from a computer tomography (CT) system, said computer and control unit comprising:
   a program memory for storing program code segments, wherein the program code segments stored in the program memory, when executed by a processor, are used to realize a method according to claim 1.

10. A non-transitory computer-readable medium including a computer program product, the computer program product comprising instructions which when executed by a processor, causes the processor to carry out functions including:
   basing an image reconstruction of an examined object from measuring data on a back projection of filtered measuring data, the measuring data being recorded with a detector during a relative movement between a radiation source of a computer tomography system and the examiner object;
   realizing the back projection using a back projection weight which depends on a location of a respective point of the image data; and
   selecting a power with which the back projection weight is used, wherein
      a differentiation according to the method of the finite differences is realized, using supporting points for filtering the measuring data,
      a distance between supporting points contain a term that depends on the location of the respective image point and corresponds to the back projection weight, and
      a power of the term follows from the power of the back projection weight.

11. A computer tomography system, comprising:
   a computer; and
   a control unit in communication with the computer, the control unit configured to carryout functions including:
      basing an image reconstruction of an examined object from measuring data on a back projection of filtered measuring data, the measuring data being recorded with a detector during a relative movement between a radiation source of the computer tomography system and the examined object,
      realizing the back projection using a back projection weight which depends on a location of a respective point of the image data, and
      selecting a power with which the back projection weight is used, wherein a differentiation according to the method of the finite differences is realized, using supporting points for filtering the measuring data, a distance between supporting points contain a term that depends on the location of the respective image point and corresponds to the back projection weight, and a power of the term follows from the power of the back projection weight.

* * * * *